United States Patent
Louis et al.

(10) Patent No.: US 7,594,931 B2
(45) Date of Patent: Sep. 29, 2009

(54) VERTEBRAL CAGE DEVICE WITH MODULAR FIXATION

(75) Inventors: Christian Louis, Aubagne (FR); Jean Huppert, L'Etrat (FR); Patrick Tropiano, Marseille (FR); Thierry Dufour, Olivet (FR)

(73) Assignee: LDR Medical, Rosieres Pres Troyes (FR)

( * ) Notice: Subject to any disclaimer, the term of this patent is extended or adjusted under 35 U.S.C. 154(b) by 588 days.

(21) Appl. No.: 10/483,563

(22) PCT Filed: Jul. 12, 2002

(86) PCT No.: PCT/IB02/03390

§ 371 (c)(1),
(2), (4) Date: May 21, 2004

(87) PCT Pub. No.: WO03/005939

PCT Pub. Date: Jan. 23, 2003

(65) Prior Publication Data

US 2004/0199254 A1   Oct. 7, 2004

(30) Foreign Application Priority Data

Jul. 13, 2001   (FR) .................................. 01 09381

(51) Int. Cl.
*A61F 2/44* (2006.01)
*A61B 17/70* (2006.01)
(52) U.S. Cl. .................................. 623/17.11; 606/247
(58) Field of Classification Search ... 623/17.11–17.16; 606/61, 247, 280
See application file for complete search history.

(56) References Cited

U.S. PATENT DOCUMENTS

| | | | |
|---|---|---|---|
| 4,714,469 A | 12/1987 | Kenna | |
| 4,997,432 A | 3/1991 | Keller | |
| 5,192,327 A | 3/1993 | Brantigan | |
| 5,246,458 A | 9/1993 | Graham | |
| 5,306,307 A | 4/1994 | Senter et al. | |
| 5,306,309 A | 4/1994 | Wagner et al. | |
| 5,397,364 A * | 3/1995 | Kozak et al. .............. | 623/17.11 |
| 5,425,772 A | 6/1995 | Brantigan | |
| 5,458,638 A | 10/1995 | Kuslich et al. | |
| 5,534,029 A | 7/1996 | Shima | |

(Continued)

FOREIGN PATENT DOCUMENTS

| FR | 2 747 034 A | 10/1997 |
|---|---|---|
| WO | 99 56676 A | 11/1999 |

OTHER PUBLICATIONS

U.S. Appl. No. 60/121,705, filed Feb. 25, 1999, Biscup.

(Continued)

*Primary Examiner*—Pedro Philogene
(74) *Attorney, Agent, or Firm*—Fish & Richardson P.C.

(57) ABSTRACT

Intervertebral arthrodesis for insertion in an intervertebral space separating opposite faces of two adjacent vertebrae has a ring shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebrae faces.

10 Claims, 5 Drawing Sheets

U.S. PATENT DOCUMENTS

| | | | |
|---|---|---|---|
| 5,554,191 A | 9/1996 | Lahille et al. | |
| 5,609,636 A | 3/1997 | Kohrs et al. | |
| 5,713,899 A | 2/1998 | Godard et al. | |
| 5,741,253 A | 4/1998 | Michelson | |
| 5,755,798 A | 5/1998 | Papavero et al. | |
| 5,766,252 A | 6/1998 | Henry et al. | |
| 5,772,661 A | 6/1998 | Michelson | |
| 5,776,199 A | 7/1998 | Michelson | |
| 5,782,919 A | 7/1998 | Zdeblick et al. | |
| 5,797,909 A | 8/1998 | Michelson | |
| 5,800,550 A | 9/1998 | Sertich | |
| 5,860,973 A | 1/1999 | Michelson | |
| 5,865,845 A | 2/1999 | Thalgott | |
| 5,888,223 A | 3/1999 | Bray | |
| 5,888,224 A | 3/1999 | Beckers et al. | |
| 5,984,967 A | 11/1999 | Zdeblick et al. | |
| 6,001,130 A | 12/1999 | Bryan et al. | |
| 6,033,438 A | 3/2000 | Bianchi et al. | |
| 6,045,579 A | 4/2000 | Hochshuler et al. | |
| 6,059,787 A * | 5/2000 | Allen | 606/75 |
| 6,063,121 A | 5/2000 | Xavier et al. | |
| 6,080,158 A | 6/2000 | Lin | |
| 6,080,193 A | 6/2000 | Hochshuler et al. | |
| 6,093,205 A | 7/2000 | McLeod et al. | |
| 6,096,038 A | 8/2000 | Michelson | |
| 6,096,080 A | 8/2000 | Nicholson | |
| 6,111,164 A | 8/2000 | Rainey et al. | |
| 6,113,637 A | 9/2000 | Gill et al. | |
| 6,113,638 A | 9/2000 | Williams et al. | |
| 6,120,502 A | 9/2000 | Michelson | |
| 6,123,705 A | 9/2000 | Michelson | |
| 6,136,031 A | 10/2000 | Middleton | |
| 6,146,421 A | 11/2000 | Gordon et al. | |
| 6,149,650 A | 11/2000 | Michelson | |
| 6,156,067 A | 12/2000 | Bryan et al. | |
| 6,179,875 B1 | 1/2001 | Von Strempel | |
| 6,193,757 B1 | 2/2001 | Foley et al. | |
| 6,206,922 B1 | 3/2001 | Zdeblick et al. | |
| 6,210,412 B1 | 4/2001 | Michelson | |
| 6,224,595 B1 | 5/2001 | Michelson | |
| 6,235,059 B1 * | 5/2001 | Benezech et al. | 623/17.16 |
| 6,241,769 B1 * | 6/2001 | Nicholson et al. | 623/17.11 |
| 6,241,770 B1 | 6/2001 | Michelson | |
| 6,245,072 B1 | 6/2001 | Zdeblick et al. | |
| 6,245,108 B1 | 6/2001 | Biscup | |
| 6,251,140 B1 | 6/2001 | Marino et al. | |
| 6,258,125 B1 | 7/2001 | Paul et al. | |
| 6,264,656 B1 | 7/2001 | Michelson | |
| 6,270,498 B1 | 8/2001 | Michelson | |
| 6,277,149 B1 | 8/2001 | Boyle et al. | |
| 6,296,664 B1 | 10/2001 | Middleton | |
| 6,302,914 B1 | 10/2001 | Michelson | |
| 6,306,170 B2 | 10/2001 | Ray | |
| 6,315,797 B1 | 11/2001 | Middleton | |
| 6,342,074 B1 * | 1/2002 | Simpson | 623/17.11 |
| 6,348,071 B1 | 2/2002 | Steffee et al. | |
| 6,350,283 B1 | 2/2002 | Michelson | |
| 6,364,880 B1 | 4/2002 | Michelson | |
| 6,371,988 B1 | 4/2002 | Pafford et al. | |
| 6,375,655 B1 | 4/2002 | Zdeblick et al. | |
| 6,395,031 B1 | 5/2002 | Foley et al. | |
| 6,395,035 B2 | 5/2002 | Bresina et al. | |
| 6,402,750 B1 | 6/2002 | Atkinson et al. | |
| 6,402,785 B1 | 6/2002 | Zdeblick et al. | |
| 6,409,765 B1 | 6/2002 | Bianchi et al. | |
| 6,419,704 B1 | 7/2002 | Ferree | |
| 6,423,095 B1 | 7/2002 | Van Hoeck et al. | |
| 6,432,106 B1 | 8/2002 | Fraser | |
| 6,432,107 B1 | 8/2002 | Ferree | |
| 6,447,512 B1 | 9/2002 | Landry et al. | |
| 6,447,544 B1 | 9/2002 | Michelson | |
| 6,447,546 B1 * | 9/2002 | Bramlet et al. | 623/17.16 |
| 6,447,547 B1 | 9/2002 | Michelson | |
| 6,454,769 B2 | 9/2002 | Wagner et al. | |
| 6,458,159 B1 | 10/2002 | Thalgott | |
| 6,461,359 B1 | 10/2002 | Tribus et al. | |
| 6,468,310 B1 | 10/2002 | Ralph et al. | |
| 6,471,724 B2 | 10/2002 | Zdeblick et al. | |
| 6,478,823 B1 | 11/2002 | Michelson | |
| 6,482,233 B1 * | 11/2002 | Aebi et al. | 623/17.11 |
| 6,500,205 B1 | 12/2002 | Michelson | |
| 6,524,312 B2 | 2/2003 | Landry et al. | |
| 6,527,806 B2 | 3/2003 | Ralph et al. | |
| 6,540,785 B1 | 4/2003 | Gill et al. | |
| 6,554,863 B2 | 4/2003 | Paul et al. | |
| 6,576,016 B1 | 6/2003 | Hochshuler et al. | |
| 6,579,291 B1 | 6/2003 | Keith et al. | |
| 6,582,468 B1 | 6/2003 | Gauchet | |
| 6,592,624 B1 | 7/2003 | Fraser et al. | |
| 6,599,320 B1 | 7/2003 | Kuslich et al. | |
| 6,605,089 B1 | 8/2003 | Michelson | |
| 6,610,089 B1 | 8/2003 | Liu et al. | |
| 6,610,092 B2 | 8/2003 | Ralph et al. | |
| 6,613,091 B1 | 9/2003 | Zdeblick et al. | |
| 6,616,671 B2 | 9/2003 | Landry et al. | |
| 6,635,087 B2 | 10/2003 | Angelucci et al. | |
| 6,645,206 B1 | 11/2003 | Zdeblick et al. | |
| 6,645,249 B2 | 11/2003 | Ralph et al. | |
| 6,652,584 B2 | 11/2003 | Michelson | |
| 6,660,038 B2 | 12/2003 | Boyer, II et al. | |
| 6,666,890 B2 | 12/2003 | Michelson | |
| 6,669,730 B2 | 12/2003 | Ralph et al. | |
| 6,669,731 B2 | 12/2003 | Ralph et al. | |
| 6,673,113 B2 | 1/2004 | Ralph et al. | |
| 6,676,703 B2 | 1/2004 | Biscup | |
| 6,679,887 B2 | 1/2004 | Nicholson et al. | |
| 6,679,915 B1 | 1/2004 | Cauthen | |
| 6,695,851 B2 | 2/2004 | Zdeblick et al. | |
| 6,695,882 B2 | 2/2004 | Bianchi et al. | |
| 6,709,458 B2 | 3/2004 | Michelson | |
| 6,716,247 B2 | 4/2004 | Michelson | |
| 6,719,794 B2 | 4/2004 | Gerber et al. | |
| 6,733,504 B2 | 5/2004 | Lin et al. | |
| 6,733,531 B1 | 5/2004 | Trieu | |
| 6,733,535 B2 | 5/2004 | Michelson | |
| 6,736,850 B2 | 5/2004 | Davis | |
| 6,740,117 B2 | 5/2004 | Ralph et al. | |
| 6,740,118 B2 | 5/2004 | Eisermann et al. | |
| 6,743,255 B2 | 6/2004 | Ferree | |
| 6,743,256 B2 | 6/2004 | Mason | |
| 6,743,257 B2 | 6/2004 | Castro | |
| 6,749,636 B2 | 6/2004 | Michelson | |
| 6,758,849 B1 | 7/2004 | Michelson | |
| 6,767,367 B1 | 7/2004 | Michelson | |
| 6,770,074 B2 | 8/2004 | Michelson | |
| 6,793,679 B2 | 9/2004 | Michelson | |
| RE38,614 E | 10/2004 | Paul et al. | |
| 6,800,092 B1 | 10/2004 | Williams et al. | |
| 6,800,093 B2 | 10/2004 | Nicholson et al. | |
| 6,964,687 B1 * | 11/2005 | Bernard et al. | 623/17.16 |
| 7,232,463 B2 * | 6/2007 | Falahee | 623/17.11 |
| 2001/0020185 A1 | 9/2001 | Ray | |
| 2002/0082597 A1 | 6/2002 | Fraser | |
| 2002/0107572 A1 | 8/2002 | Foley et al. | |
| 2002/0151893 A1 | 10/2002 | Santilli | |
| 2002/0193880 A1 | 12/2002 | Fraser | |
| 2003/0028249 A1 | 2/2003 | Baccelli et al. | |
| 2003/0109928 A1 | 6/2003 | Pasquet et al. | |
| 2003/0167091 A1 | 9/2003 | Scharf | |
| 2003/0195626 A1 | 10/2003 | Huppert | |
| 2003/0195632 A1 | 10/2003 | Foley et al. | |
| 2003/0204260 A1 | 10/2003 | Ferree | |
| 2004/0073309 A1 | 4/2004 | Bianchi et al. | |
| 2004/0127993 A1 | 7/2004 | Kast et al. | |

| | | |
|---|---|---|
| 2004/0127994 A1 | 7/2004 | Kast et al. |
| 2004/0148029 A1 | 7/2004 | Bianchi et al. |
| 2004/0162617 A1 | 8/2004 | Zucherman et al. |
| 2004/0172130 A1 | 9/2004 | Nakahara et al. |
| 2004/0199254 A1 | 10/2004 | Louis et al. |
| 2005/0038511 A1 | 2/2005 | Martz et al. |

OTHER PUBLICATIONS

FR 2 808 995 Preliminary Search Report, National Institute of Industrial Property (France), Jan. 29, 2001.

FR 2 827 156 Preliminary Search Report, National Institute of Industrial Property (France), Apr. 5, 2002.

Greffe et fusion, Website: http://www.ldrmedical.fr/roi.htm, Sep. 19, 2004.

Mc+ Le choix de l'ancrage, Website: http://www.ldrmedical.fr/mcplus.htm, Sep. 19, 2004.

PCT/FR01/01545, International Preliminary Examination Report, EPO, Aug. 30, 2002.

PCT/FR01/01545, International Search Report, EPO, Sep. 5, 2001.

PCT/IB02/03390, International Preliminary Examination Report, EPO, Nov. 6, 2003.

PCT/IB02/03390, International Search Report, EPO, Mar. 3, 2003.

ROI Privilegier la greffe en creant la chambre de fusion, Website: http://www.ldrmedical.fr/roi.htm, Sep. 19, 2004.

* cited by examiner fig. 2a fig. 3a fig. 3b fig. 4a fig. 3c

VERTEBRAL CAGE DEVICE WITH MODULAR FIXATION

The present invention concerns an arthrodesis device, used to enable fusing of two contiguous vertebrae by development of bony tissues with replacement of fibrocartilaginous discs ensuring the bonding between the vertebrae of the vertebral column or the end of the latter.

The intervertebral discs are formed from a deformable but not compressible part called "nucleus pulposus" containing approximately 80% water, surrounded by several elastic fibrous layers uniting to maintain the nucleus, absorbing part of the forces applied to the disc unit, and stabilizing the articulation. These parts may often be degraded by compression, displacement or wear and tear, following shocks, infections, exaggerated forces or simply over time. The degradation of this articulation part may cause intense pain in the patient and significant discomfort.

In a good number of cases, the treatment consists of removing all or part of the damaged intervertebral disc and connecting the vertebrae concerned by causing bony fusion between them. To do that, one places between the vertebrae an artificial structure allowing their separation to be maintained, while with it introducing into the intervertebral space either a bony graft or a bony substitute, compounded material that will be invaded by the growth of adjacent bony tissues. This structure often takes the shape of an open or closed ring called cage, and may be positioned on the basis of a cage by the intervertebral space in the case of cervical vertebrae, or on the basis of one or two cages by the intervertebral space in the case of lumbar vertebrae. This positioning is done most often by the anterior surface of the vertebrae in the case of a cervical cage, or by the anterolateral surface of the vertebrae (one cage) or posterior (two cages) of vertebrae in the case of a lumbar cage. As for grafts and bony substitutes, they are introduced in the cage either before or after its positioning and are therefore found in contact with the two vertebrae surrounding the treated intervertebral space.

During the time necessary for growth and up to the reinforcement of arthrodesis, which may be on the order of six months, it is important that the various movements of forces taking place in the intervertebral space do not cause displacement of the cage, which would then risk deteriorating the bony tissues during formation or even escaping outside this space and damaging the adjacent organs.

To avoid such displacements, a solution used consists of equipping the surfaces of the cage in contact with the vertebrae with varieties of shape such as saw tooth notches as described in the patents FR0006351 or FR2733413. Such a solution however proves to be insufficient in a certain number of cases.

Another solution consists of equipping the cage with a flange that extends on the outside of the intervertebral space and is applied on the side of each of the two contiguous vertebrae, to which it is fixed by a bone anchoring screw. Such a solution has been used since about 1988 and is described for example in the patent FR 2 747 034. Such a plate however represents an overcrowding outside the intervertebral space that sometimes may pose problems in particular in the case of arthrodesis of the cervical vertebrae where the space available is very limited. In fact, the presence of the plate may for example form a daily discomfort for the patient or form an immediate or future obstacle in the positioning of another cage with plate in one of the immediately adjacent plates.

Furthermore, in particular in the case of cervical vertebrae, the movements of the spine often have the tendency to cause loosening of the bone anchoring screws, which decreases the effectiveness of such a plate and may also cause damages to the organs surrounding the plate.

Therefore, it is worthwhile to also provide for a system enabling fixation of the cage without a part extending outside the intervertebral space.

Moreover, these different solutions may fulfil the needs of an arthrodesis operation differently without it being necessarily possible to know in advance which will be preferable. Therefore, it is easier and less expensive to provide for a modular device comprising interchangeable parts for achieving different solutions.

SUMMARY OF THE INVENTION

To remedy some of these drawbacks, the present invention proposes an intervertebral arthrodesis device designed to be inserted in an intervertebral space separating the opposite plates of the two adjacent vertebrae, characterised in that it comprises at least one structure called intervertebral cage presenting the shape of a ring that may or may not be open, in which at least one part, along the axis of the spine, has a lower height than the rest of this same cage and forms a small bar crossed by at least one drilling of the axis approximately perpendicular to the plate of at least one of the adjacent vertebrae.

According to one characteristic, the device includes at least one intervertebral cage having on its surfaces in contact with the vertebrae, undulations in shape limiting its possibilities for sliding in a plane parallel to said vertebrae.

According to one characteristic, the device comprises at least one fixation structure for fixedly mounting the cage(s) to at least one of these vertebrae. The fixation structure can be added to at least one intervertebral cage by insertion of a projecting part in at least one bore or opening of the cage.

According to one characteristic, the fixation structure includes at least two bone anchoring pins with approximately parallel axes. The pins are connected together by a small rod, and extend through openings or bores of the small rod of the cages. The pins extending through the opening are pushed into a face of at least one vertebra to keep the cage in position in the intervertebral space.

According to one characteristic, at least one of the bone anchoring pins of the fixation structure includes reliefs for limiting the possibilitites of the cage sliding outside the face where it is impacted.

According to one characteristic, the fixation structure comprises at least one fixation plate fixed to the external surface of at least one vertebra and including at least one opening or bore for receiving a bone anchoring screw fixed to this same vertebra.

According to one characteristic, at least one of the openings of the fixation plate presents in the plane of this plate a section at the level of its opening opposite the vertebra that is not as high as in its part located within the thickness of the plate. A bone anchoring screw has a head which presents at least one part of a section greater than that of the opening of the plate and is thus retained within this same opening by this same external opening.

According to one feature the fixation structure includes at least two locking studs with approximately parallel axes connected by a small rod. These locking studs are inserted into at least one hole or bore of at least one intervertebral cage to lock said fixation structure to said cage and to keep the cage in position in the intervertebral space.

According to one feature, at least one of the ends of the small rod has at least one protuberance clipped in at least one housing arranged in the wall of the intervertebral cage so as to limit or prevent the movements of this same rod relative to this same cage.

According to one characteristic, the fixation structure comprises a fixation plate (called a hemiplate) coupled to the exterior surface of at least one vertebra. The fixation plate structure includes at least one opening or bore through which is inserted a bone anchoring screw fixed in other vertebra to keep said cage in position in the intervertebral space.

According to one feature, the fixation hemiplate with the small rod connecting the anchoring pins or the locking studs forms a piece with an "L" section.

According to one characteristic, the fixation structure comprises a fixation plate (called complete) coupled to the exterior surface of at least two vertebra. Near each end of the plate there is at least one bore or opening through which is inserted a bone anchoring screw that is fixed in said vertebrae to prevent any migration of the intervertebral cage within or outside the intervertebral space.

According to one characteristic, the complete fixation plate with the small rod connects the anchoring pins or the locking studs with a "T" section.

According to one feature, the fixation plate includes an opening at the level of the intervertebral space. This opening enables the introduction or packing of a graft or bone substitute in the intervertebral space after insertion of the device.

According to one characteristic, each bore in the fixation structure acts with a bone anchoring screw. When the anchoring screw is in place, it is located in a position shifted relative to a plane containing the axis of the spine.

According to one feature, at least one intervertebral cage has, along the axis of the spine, a nonuniform height. This variation in height induces a determined angle between the vertebra faces with respect to the adjacent vertebrae.

According to one characteristic, at least one of the constitutive parts of the device is made from a radiotransparent material.

BRIEF DESCRIPTION OF THE DRAWINGS

The invention, with its characteristics and advantages, will be more clearly evident with the reading of the description made in reference to the fixed drawings in which.

DETAILED DESCRIPTION OF THE DRAWINGS

Reference is now made to the Figures wherein is illustrated ring shaped intervetrbral cage (1), designed to be inserted in the intervertebral space (E) to be treated between two contiguous vertebrae, and to be received into an interior cavity (10, FIG. 2a) a bony material acting as a graft, or any structure that can act as a bony substitute or be "assembled" by a growth of bony material. The cavity of the intervertebral cage can thus be filled before or after it is positioned in the intervertebral space.

According to some applications, the device includes a single intervertebral cage (FIGS. 1 and 2a), for example to carry out arthrodesis between two cervical vertebrae. It is to be understood that for other applications, the device can include two intervertebral cages (not represented), for example, to carry out arthrodesis between two lumbar vertebrae during postioning by the posterior route.

According to the applications, an intervertebral cage according to the invention may be made in the shape of a closed ring (1, FIG. 3a) or in the form of a ring opened on one side (not represented).

Figure 1A:
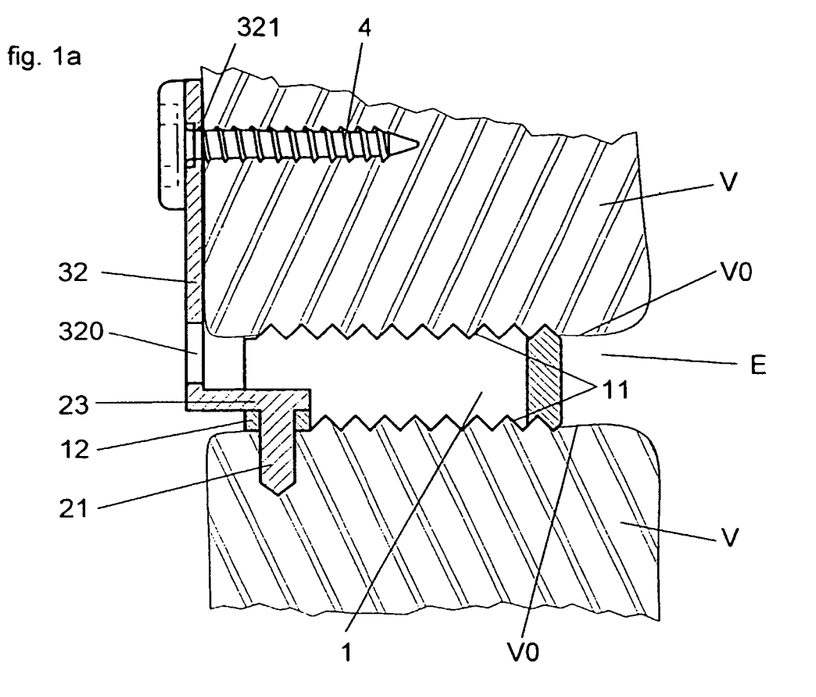
FIG. 1a is a side sectional view of the device according to the invention in an embodiment where the fixation device comprises anchoring pins and a top hemiplate.
Figure 1B:
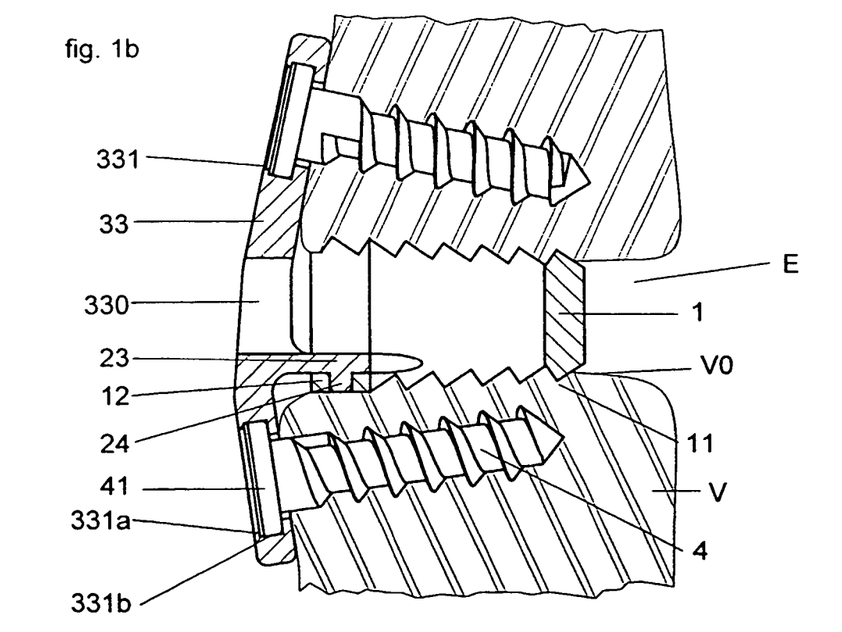
FIG. 1b is a side sectional view of the device according to the invention in an embodiment where the fixation device comprises a complete plate, with opening, added by locking studs and with anchoring screws retained in the openings or bores of the plate.
Figure 2A:
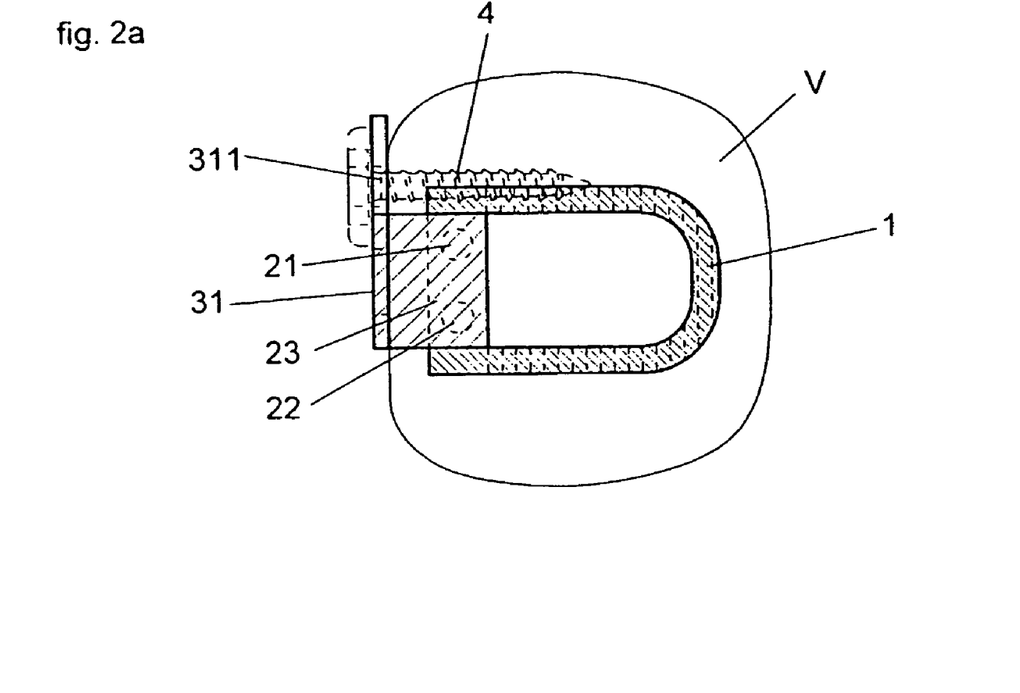
FIG. 2 is a top sectional view of the device according to the invention in an embodiment where the fixation device comprises anchoring pins and a low hemiplate.

In one embodiment represented in FIGS. 1 and 2a, the invention comprises a fixation device enabling its anchoring in the plate (V0) of a vertebra (V) within the intervertebral space (E) to be treated. This fixation device is formed from two anchoring pins (21, 22), with approximately parallel axes and connected by a small rod (23). These anchoring pins are introduced into two drillings (121, 122) made in a thinned down part of the intervertebral cage, then are impacted, that is pushed in with force, into the bony material forming the plate of one of the two vertebrae surrounding the intervertebral space to be treated.

In one embodiment, the thinned down part of the cage forms a small flat rod (12) that abuts small flat rod (23), connecting the two anchoring pins (21, 22) when the latter are impacted in face (V0) of a vertebra (V). The thickness of the small rod (23) connecting the anchoring pins and the small rod (12) formed by a thinning of the intervertebral cage (1) are such that the superimposition of the two small rods (12, 23) after impacting is no higher along the axis of the spine than the rest of the intervertebral cage (1).

Figure 3A:
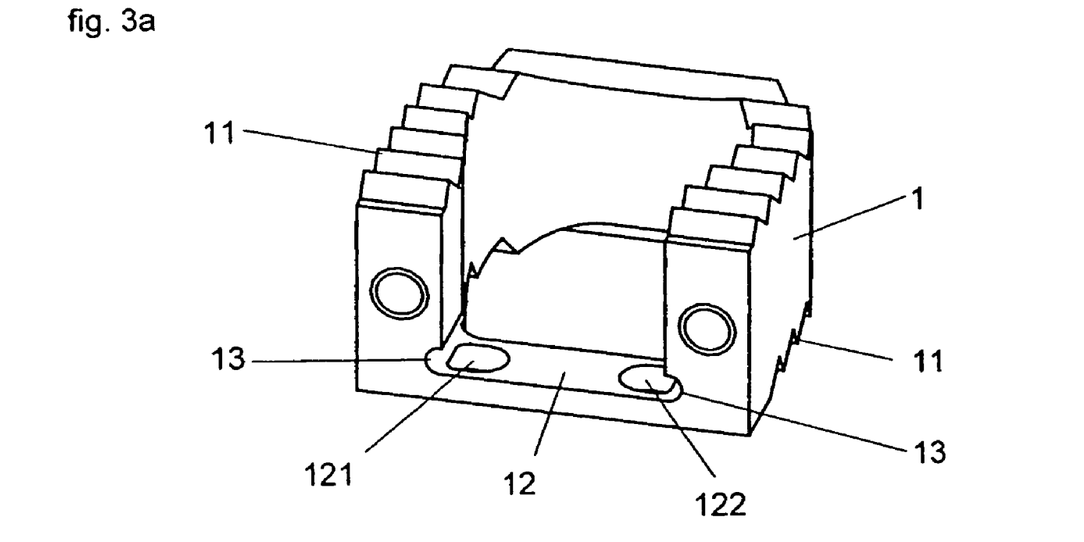
FIG. 3a is a perspective view of an intervertebral cage according to a preferred embodiment of the invention.
Figure 3B:
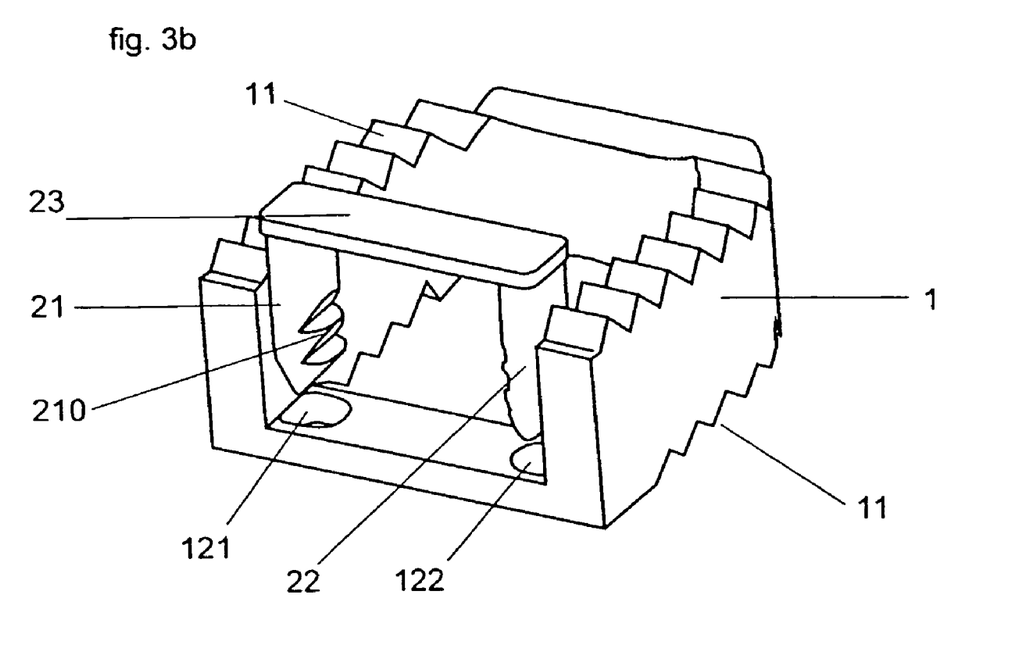
FIG. 3b is a perspective view of a device according to a preferred embodiment of the invention before insertion of impacting pins in an embodiment where the fixation device comprises anchoring pins with undulations in shape.

In one embodiment represented in FIG. 3b the length of the anchoring pins (21, 22) and the thickness of the small rod (23) connecting them are determined so that the sum of these two dimensions forming the height of the fixation device in this embodiment is no greater than the height along the axis of the spine of the rest of the intervertebral cage (1). Thus, it is possible to introduce into this intervertebral space an intervertebral cage already provided with anchoring pins, the latter then only having been impacted into the face (V0) of a vertebra (V), for example with the aid of a spreader, a distractor or another tool of known type.

Figure 3C:
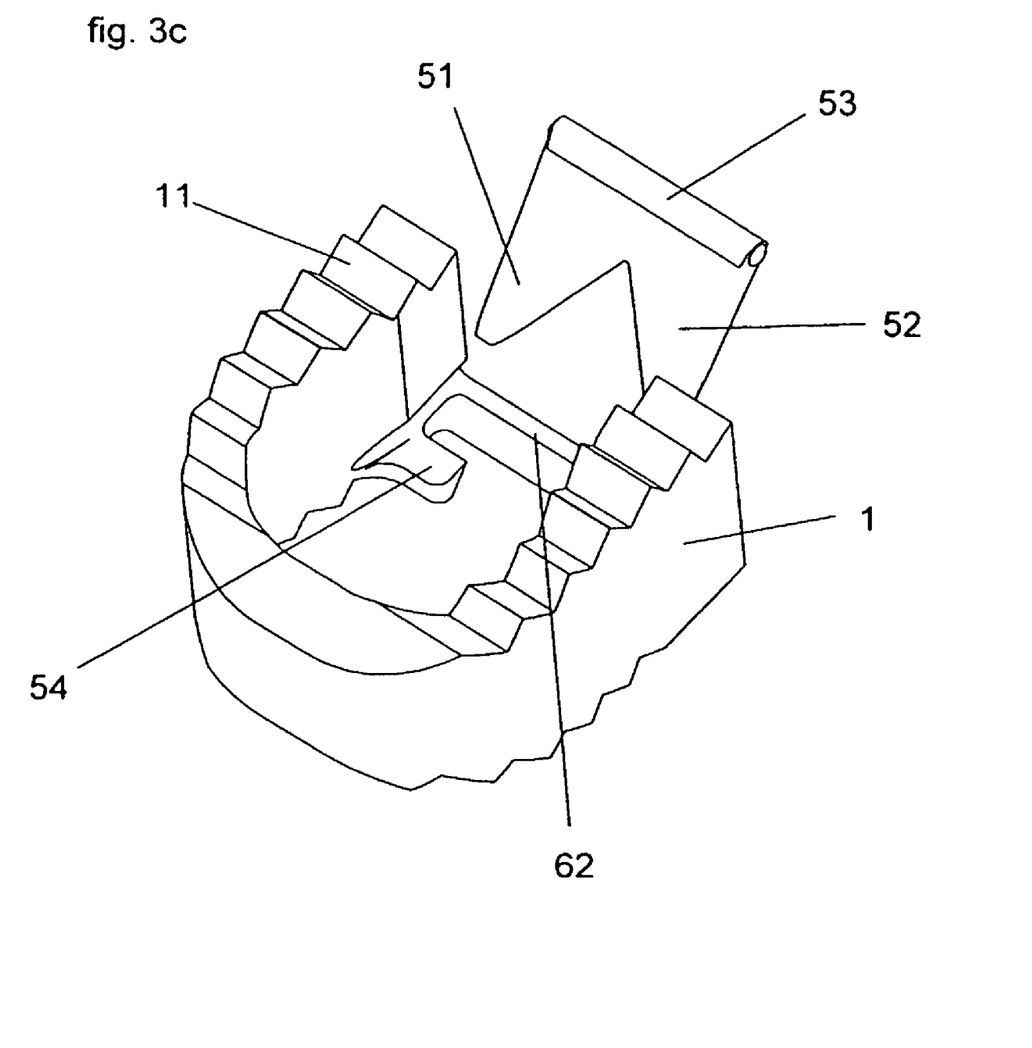
FIG. 3c is a perspective view of a device according to a preferred embodiment of the invention before impacting tongues in an embodiment, where the fixation device comprises anchoring tongues.

In one embodiment represented in FIG. 3c, the fixation device, enabling the device to be anchored in the face (V0) of a vertebra (V) within the intervertebral space (E) to be treated, is constituted of an anchoring tongue including legs (51, 52) having intersecting edges forming a "V" are connected by a small rod (53). Legs (51, 52) are introduced between a thinned down part of the intervertebral cage formed by a small rod (62) and two lugs (only one, 54, is represented on FIG. 3c) formed on the device and symmetrically disposed in relation to the device axis. The "V" shaped anchoring tongue including legs (51, 52) is then forced into place similarly to the device provided with pins (21, 22). Legs (51, 52) are forced into place in face V0 of vertebra V so the small flat rod (53), connecting the anchoring legs (51, 52), abuts small flat rod (62). The diameters of the small rod (53) connecting the anchoring tongues and the small rod (62) formed by a thinning of the intervertebral cage (1) are such that the superimposition of the two small rods (62, 53) after legs (51, 52) are forced into face (V0) is no higher along the axis of the spine than the rest of the intervertebral cage (1).

In one embodiment (not shown), the device according to the invention comprises two intervertebral cages. Each of the two cages is formed from an open ring having at least one part having a reduced height along the axis of the spinal cord. In one embodiment, at least one of the cages is in the shape of a "U" or "C" (not shown). Each cage includes at its end a small rod from one part having a reduced height along the axis of the spine. These small rods are crossed by at least one bore or opening having an axis approximately perpendicular to the face (V0) of the vertebra (V) with which they are in contact. In one embodiment, two intervertebral cages are arranged in the intervertebral space with their openings facing each other. At least one fixation device including two anchoring pins with parallel axes connected by a small rod is introduced into the bore of each of the two small rods with ends facing each other. The anchoring pins are then forced into the face of the vertebra and inserted into the bores of the small rods of the intervertebral cages to help to keep said cages immovable.

In one embodiment, an intervertebral cage (1) used in a device according to the invention has at least one undulating surface (11) in contact with the vertebrae; in one example the undulating contact surface (11) has a saw tooth shape as illustrated in FIG. 3c. Under the pressure exerted by the vertebrae surrounding the treated intervertebral space (E), the undulating surface (11) supports the surface of faces (V0) of these same vertebrae to limit the risks of displacement of the intervertebral cage.

Figure 4A:
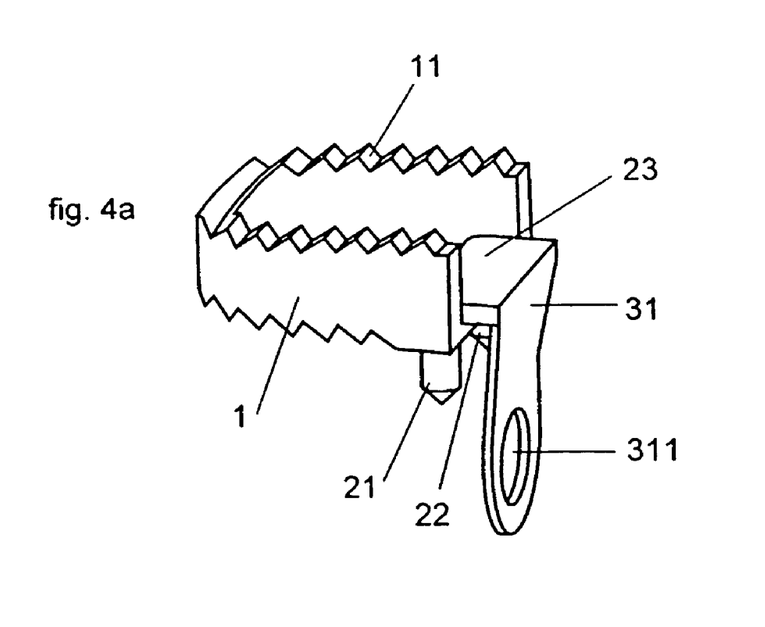
FIG. 4a is a perspective view of a device according to a preferred embodiment of the invention where the fixation device comprises anchoring pins and a low hemiplate.
Figure 4B:
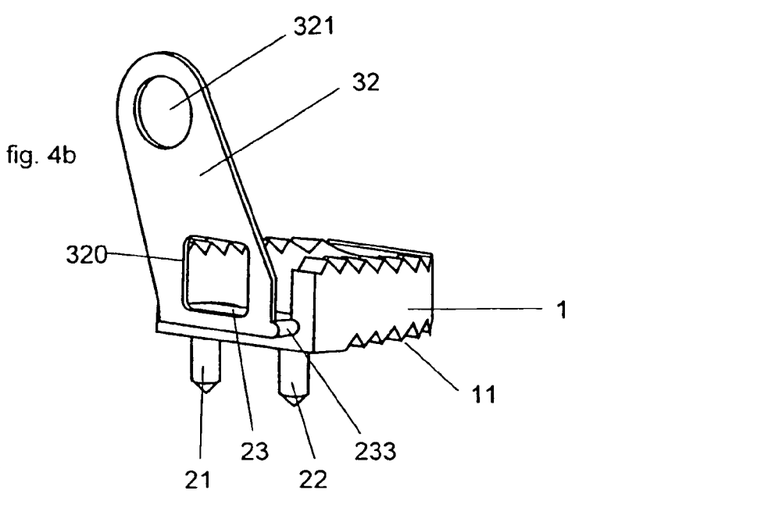
FIG. 4b is a perspective view of a device according to a preferred embodiment of the invention where the fixation device comprises anchoring pins and a top hemiplate with an opening.

In one embodiment, represented in FIGS. 1, 2a and 4b, a fixation device comprises a plate called top hemiplate (32), united with the small rod (23) connecting the anchoring pins (21, 22) to each other. Hemiplate (32) extends outside the intervertebral space (E) to be treated and is coupled to the exterior surface of the vertebra opposite the vertebra receiving the anchoring pins. This top hemiplate (32) includes at least one bore or opening (321) which receives a bone anchoring screw (4) of a known type. Screw (4) is fixed in the body of the vertebra and inserted in the face(V0) to prevent any migration of the intervertebral cage (1) within or outside the treated intervertebral space (E). Top hemiplate (32) also comprises an opening (320) enabling introduction of the graft into the cage (1) after the cage is positioned in the intervertebral space. The part of the piece connecting the small rod (23) and the top hemiplate (32) has an "L" shape.

In one embodiment represented in FIG. 4a, a plate called bottom hemiplate (31), is fixed in the same way to the vertebra receiving the anchoring pins. The part of the piece connecting the small rod (23) and the bottom hemiplate (31) has an "L" shape.

Figure 5A:
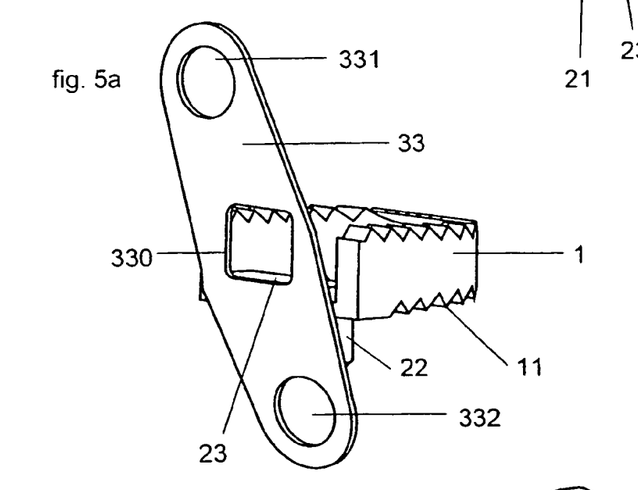
FIG. 5a is a perspective view of a device according to a preferred embodiment of the invention where the fixation device comprises anchoring pins and a complete plate with an opening.

In one embodiment represented in FIG. 5a, a fixation device comprises a plate called complete plate (33) that is integral with the small rod (23) connecting the anchoring pins (21, 22) to each other. Plate (33) extends to the exterior of the intervertebral space (E) to be treated and is coupled to the exterior surface of these two vertebrae surrounding the intervertebral space (E) to be treated. The part of the piece connecting the small rod (23) and the complete plate (33) has a "T" shape. Complete plate (33) includes at least two bores (331, 332), each of which receives a bone anchoring screw (4) of a known type. Screw (4) is fixed in the body of the corresponding vertebra and inserted in the plate (33) to prevent any migration of the intervertebral cage (1) within or outside the treated intervertebral space (E). This complete plate (33) also comprises an opening (330) enabling introduction of the graft into the cage (1) after the cage is placed in the intervertebral space.

Figure 5B:
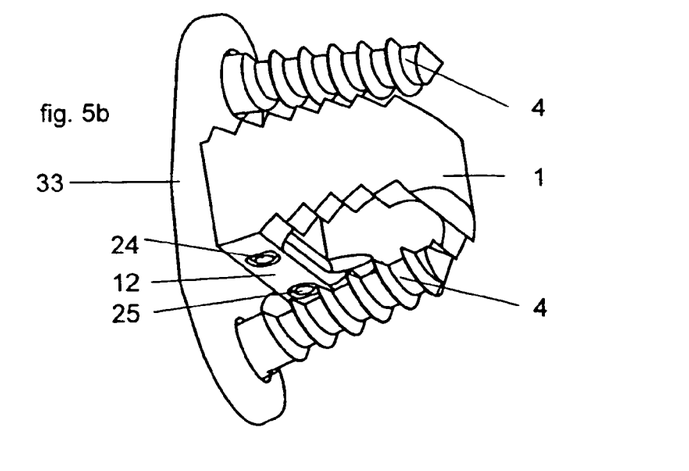
FIG. 5b is a perspective view of a device according to a preferred embodiment of the invention where the fixation device comprises a complete plate added by locking studs, illustrated with anchoring screws.

In one embodiment represented in FIGS. 1b, 5a and 5b, a fixation device comprises a plate called complete plate (33) united with the small rod (23). Small rod (23) includes two locking studs (24, 25) perpendicular to the longitudinal axis of rod (23). Studs (24, 25) are housed in the two bores (121, 122) of the intervertebral cage (1). This complete plate (33) extends outside the intervertebral space (E) to be treated and is coupled to the exterior surface of the two vertebrae surrounding the intervertebral space (E) to be treated. The use of locking studs (24, 25) rather than pins makes it possible to use a softer material that is forced into the face of the vertebra, but on the other hand has the advantage of being transparent during radiography. The part of the piece connecting the small rod (23) and the complete plate (33) has a "T" shape in its section along a plane containing the axis of the spine.

This complete plate (33) includes at least two bores (331, 332) each of which receives a bone anchoring screw (4) of a known type. Screw (4) is fixed in the body of the corresponding vertebra and inserted into the face of the vertebra to prevent migration of the intervertebral cage (1) within or outside the treated intervertebral space (E).

In the embodiment illustrated in FIGS. 3a and 5a, each of the two opposite ends of small rod (23) connecting the locking studs and the complete plate (33) has a rounded protuberance contacting the walls of the intervertebral cage (1). The rounded protuberances are clipped by elastic deformation in a housing (13) arranged in the wall opposite the intervertebral cage (1). The clipping of the protuberances (233) in the housings (13) makes it possible to maintain the cage (1) and the plate (33) together during positioning of the unit or after positioning.

In one embodiment, to prevent the anchoring screws from loosening, for example under the effect of the movements of the spine, the bores in plate (33) that receive the screws in a plane parallel to the plate (33) have a section slightly lower than the interior of the plate at the level of their opening on the surface opposite the vertebra; the surface opposite the vertebrae is called an external surface area. The heads of the screws have a part of a section greater than that of the external opening of the bore. Thus, once the screw has been screwed to where the large part of the head of the screw has penetrated the interior of the bore under force, the elasticity of the material forming the plate retains the screw head within the bore, limiting the risks of later loosening. This complete plate (33) also comprises an opening (330) enabling introduction of the graft into the cage (1) after positioning of the cage in the intervertebral space.

In one embodiment the plate (31, 32, 33) of the fixation device includes at least one bore (311, 321, 331, 332) for receiving a bone anchoring screw (4) which is located in a position shifted relative to a plane containing the axis of the spine. Thus, it is possible to treat two adjacent intervertebral spaces by using fixation plates and by positioning these plates in staggered rows. The shifted position of the bores in the plates enables the plates to be fixed in place by different screws located on the same vertebra and at the same height along the axis of the spine.

In one embodiment, all or part of the device according to the invention is made from a radiotransparent material, for example from PEEK, which makes it possible to monitor the development of bony tissues within the cage by radiography. In spite of that, for verification that the elements of the device are not displaced, it is possible to fix one or more of the elements with a radio marker containing, for example, a small piece of non-radiotransparent material.

Therefore, according to the applications it is possible to position an intervertebral cage (1) in different ways, simply by using one type or another of fixation device. The same intervertebral cage (1) can, for example, be positioned:
- either alone,
- or provided with a fixation device with pins (21, 22, 23),
- or provided with a fixation device with pins and a top (32) or bottom (33) hemiplate,
- or provided with a fixation device with pins and with a complete plate (33),
- or provided with a top (32) or bottom (31) hemiplate added by locking studs (24, 25),
- or provided with a complete plate (33) added by locking studs (24, 25).

Such modularity makes it possible for the surgeon to choose the type of fixation during the surgery and according to the anatomic conditions he encounters, by having at his disposal a reduced number of components among which to choose.

The fixation device that includes pins or a plate or both, can be later removed (for example during a new surgery) without significant destruction of the arthrodesis. In fact, this device may no longer be necessary after reinforcement of the arthrodesis, although providing discomfort, either for the patient or for similar treatment of an adjacent intervertebral space.

It must be obvious for persons skilled in the art that the present invention makes possible embodiments under numerous other specific forms without leaving the field of application of the invention as claimed. As a result, the present embodiments must be considered as illustration, but may be modified in the field defined by the scope of the fixed claims, and the invention must not be limited by the details given above.

The invention claimed is:

1. Intervertebral arthrodesis device having a size and shape for insertion in an intervertebral space separating opposite faces of two adjacent vertebrae comprising at least one intervertebral cage substantially in the shape of a ring which may be open along a side and having a bar adapted to extend perpendicular to the axis of the spine when the arthrodesis device is inserted in the intervertebral space, the bar having a height less than another portion of the cage, and a fixation structure for securing the at least one cage to at least one of the vertebrae, the fixation structure being arranged to be added to the at least one intervertebral cage by inserting a projecting part of the fixation structure through at least one opening extending along the bar, the fixation structure including at least two locking studs with approximately parallel axes connected by a small rod, the locking studs being insertable into at least one opening of at least one intervertebral cage to lock the fixation structure to the cage and to keep the cage in position in the intervertebral space, and at least one of the ends of the small rod has at least one protuberance clipped in at least one housing arranged in the wall of the intervertebral cane for limiting or preventing movements of said rod relative to said cage.

2. Device according to claim 1 wherein the ring is closed.

3. Device according to claim 1 wherein the ring includes an open segment.

4. Device according to claim 1 wherein at least one intervertebral cage includes on its surfaces adapted to contact the vertebrae an undulating shape for limiting sliding of the cage in a plane parallel to the faces of said vertebrae.

5. Device according to claim 1 wherein the fixation structure comprises a fixation hemiplate coupled to the exterior surface of at least one vertebra, the fixation hemiplate including at least one opening through which is inserted a bone anchoring screw for attachment in said vertebra to keep said cage in position in the intervertebral space.

6. Device according to claim 1 wherein the fixation structure comprises a complete fixation plate adapted to be coupled to the exterior surface of at least two vertebrae, the complete fixation plate including near each end at least one opening through each of which is adapted to be inserted into a bone anchoring screw adapted to be fixed in said vertebrae to prevent any migration of the intervertebral cage within or outside the intervertebral space.

7. Device according to claim 6 wherein the fixation plate includes an opening at the level of the intervertebral space, said opening enabling the introduction or packing of a graft or bony substitute in the intervertebral space after insertion of the device.

8. Device according to claim 5 wherein each of the openings of the fixation structure acts together with a bone anchoring screw so that once in place the fixation structure is located in a position shifted relative to a plane containing the axis of the spine.

9. Device according to claim 1 wherein the at least one intervertebral cage has, along the axis of the spine, a non-uniform height, the non-uniform height inducing a determined angle between the faces of the vertebrae with respect to the adjacent vertebrae.

10. Device according to claim 1 wherein at least one of the constitutive parts of the device is made from a radiotransparent material.

* * * * *

UNITED STATES PATENT AND TRADEMARK OFFICE
CERTIFICATE OF CORRECTION

PATENT NO.        : 7,594,931 B2                                      Page 1 of 1
APPLICATION NO.   : 10/483563
DATED             : September 29, 2009
INVENTOR(S)       : Christian Louis et al.

It is certified that error appears in the above-identified patent and that said Letters Patent is hereby corrected as shown below:

Column 8, line 16 delete "cane" and insert --cage--, therefore.

Signed and Sealed this

Seventeenth Day of November, 2009

David J. Kappos
*Director of the United States Patent and Trademark Office*